United States Patent [19]

Ando et al.

[11] 4,259,524
[45] Mar. 31, 1981

[54] METHOD FOR PRODUCING DIBASIC FATTY ACID USING LIQUID NITROGEN DIOXIDE ($N_2O_4$) AS REACTING AGENT

[75] Inventors: Wataru Ando, Sakura; Ichiro Nakaoka, Machida, both of Japan

[73] Assignee: K.K. Pollution Preventing Research Laboratory, Tokyo, Japan

[21] Appl. No.: 55,591

[22] Filed: Jul. 9, 1979

Related U.S. Application Data

[63] Continuation of Ser. No. 868,294, Jan. 10, 1978, abandoned, which is a continuation of Ser. No. 717,179, Aug. 24, 1976, abandoned.

[30] Foreign Application Priority Data

Aug. 27, 1975 [JP] Japan .............................. 50-103071
Jul. 6, 1976 [JP] Japan .............................. 51-79445

[51] Int. Cl.³ ................... C07C 51/27; C07C 51/275; C07C 51/245
[52] U.S. Cl. .................................. 562/526; 562/528; 562/540
[58] Field of Search ............... 562/526, 528, 540, 520

[56] References Cited

U.S. PATENT DOCUMENTS

| | | | |
|---|---|---|---|
| 2,298,387 | 10/1942 | Kenyon et al. | 562/527 |
| 2,459,690 | 1/1949 | Doumani et al. | 562/527 |
| 2,465,984 | 3/1949 | Doumani et al. | 562/527 |
| 2,811,546 | 10/1957 | Robertson et al. | 562/527 |
| 3,366,680 | 1/1968 | Minisci et al. | 562/527 |
| 3,444,194 | 5/1969 | Minisci et al. | 562/527 |
| 3,631,097 | 12/1971 | Christmann et al. | 562/527 |

FOREIGN PATENT DOCUMENTS

41-20618 12/1966 Japan .
45-487 1/1970 Japan .
48-23417 7/1973 Japan .
51-18925 6/1976 Japan .

*Primary Examiner*—Paul J. Killos
*Attorney, Agent, or Firm*—Fitzpatrick, Cella, Harper & Scinto

[57] ABSTRACT

A method for the oxidation of alicyclic hydrocarbons having substituent groups by the use of liquid nitrogen dioxide ($N_2O_4$).

4 Claims, No Drawings

METHOD FOR PRODUCING DIBASIC FATTY ACID USING LIQUID NITROGEN DIOXIDE (N₂O₄) AS REACTING AGENT

This is a continuation, of application Ser. No. 868,294, filed Jan. 10, 1978, now abandoned, which is a continuation of 717,179, filed Aug. 24, 1976, now abandoned.

BACKGROUND OF THE INVENTION a. Field of the Invention

This invention relates to a method of the oxidation of alicyclic hydrocarbons having therein substituent groups by the use of liquid nitrogen dioxide ($N_2O_4$).

b. Description of Prior Arts

Oxidizing agents to be used for the oxidation reaction of organic substances are those selected from inorganic peroxides, organic peroxides, nitric acid, oxygen, or gases containing therein molecular oxygen (e.g., air), and so forth. For the purpose of this reaction, a catalyst is used in the main.

There have been known various methods for producing adipic acid in accordance with conventional techniques. For its production in an industrial scale, there have been adopted two major methods of: (1) hydrogenating acrylonitrile in an electro-chemical manner, followed by dimerizing the same to produce dinitrile, and then hydrolyzing dinitrile to obtain adipic acid; and (2) hydrogenating and dimerizing acrylic acid in dimethyl sulfoxide as the solvent by using sodium amalgam to obtain adipic acid. However, methods which are still predominant as the major production system in a large industrial scale are those which utilize cyclohexane as the starting material to be oxidized into adipic acid. Representative of such methods are as follows.

(a) "Chemical Technology", 1974 (9), pp. 555–559 discloses a method for producing adipic acid by oxidizing cyclohexane with molecular oxygen under pressure by the use of a solvent, a reaction initiator, and a catalyst.

(b) "Encyklopaedie der technischen Chemie" by Ulmann, 1953, Vol. 3, page 95 describes a method for producing adipic acid by oxidizing cyclohexane with nitric acid under pressure.

(c) "Encyklopaedic der technischen Chemie" by Ulmann, 1973, Vol. 7, page 108 describes a method for producing adipic acid indirectly from cyclohexane, wherein the acid is obtained by first oxidizing cyclohexane with molecular oxygen under pressure in the presence of a catalyst to thereby produce a mixture of cyclohexanol and cyclohexanone, and immediately oxidizing this mixture with molecular oxygen under pressure, or oxidizing each of the abovementioned components, after it is separated from the mixture, with molecular oxygen under normal pressure in the presence of a catalyst, whereby obtaining adipic acid. As another method, cyclohexanone is oxidized with nitric acid in the presence of a catalyst.

Besides the abovementioned methods of producing adipic acid in an industrial scale, the below-listed methods are known.

(d) Japanese Patent Publication No. 39-3812; "Industrial and Engineering Chemistry Design and Development", Vol. 4, No. 4, 1965, pp. 411–420; and "Industrial and Engineering Chemistry", Vol. 47, No. 4, 1955, pp. 782–785 describe method of producing adipic acid by the radical reaction, wherein cyclohexane is oxidized with nitrogen dioxide ($NO_2$) in the presence, or absence, of a catalyst.

(e) Japanese Patent Publication No. 44-24094; and Japanese Patent Application No. 51-39270 (filed April 9, 1976) disclose reactions to produce adipic acid, wherein cyclohexane is oxidized with nitrogen dioxide ($NO_2$) under irradiation of ultra-violet rays. The abovementioned Japanese Patent Application No. 51-39270 was filed by the applicants of the present application, the content of which is a photo-chemical reaction between nitrogen dioxide and cyclohexane with particular importance being attached to the presence of oxygen.

Next, the known methods for producing 1,10-decanedicarboxylic acid are as follows.

(f) "Chemical Abstract", Vol. 84, No. 9, 1976, 58652g discloses that 1,10-decanedicarboxylic acid is produced at a rate of yield of 88% by oxidizing cyclododecanol, or cyclododecanone, or a mixture of both, with nitric acid using vanadium and its compounds, or antimony and its compounds as the catalyst, to thereby open the ring.

(g) "Chemical Abstract", Vol. 84, No. 11, 1976, 73659r discloses the 1,10-decanedicarboxylic acid is produced, at a rate of selection of 94 to 96% and at a rate of conversion of 20 to 30%, by oxidizing cyclododecane with ozone-containing oxygen or air in nitromethane as the solvent, and in the presence of manganese acetate as the catalyst, to thereby open the ring.

(h) Japanese Patent Application No. 43-40195 (filed June 13, 1965) describes that adipic acid is produced from cyclohexene, and that suberic acid is produced from cyclooctane, according to which cyclo-alkene having the carbon atoms of from 5 to 12 ($C_5$–$C_{12}$) is oxidized with oxygen or gases containing therein molecular oxygen under pressure, using a lower carboxylic acid as the solvent and a salt of mercury or nickel, chromium, zinc (Ni.Cr.Zn) as the catalyst to open the ring, thereby obtaining dibasic fatty acids corresponding to the respective carbon atoms.

SUMMARY OF THE INVENTION

The present invention proposes a first method for oxidizing and ring-opening of an alicyclic hydrocarbon compound having a substituent group by adding it directly or dissolved in an inert organic solvent to liquid nitrogen dioxide ($N_2O_4$) or liquid nitrogen dioxide ($N_2O_4$) in an inert organic solvent, at substantially anhydrous conditions, in the absence of catalyst. In concrete, the method concerns with oxidizing and ring-opening of cycloalkane derivatives of carbon atoms of from 5 to 12 ($C_5$–$C_{12}$) having therein substituent groups.

The present invention proposes also a second method for oxidizing and ring-opening of an alicyclic hydrocarbon compound having a substituent group by adding liquid nitrogen dioxide ($N_2O_4$) or liquid nitrogen dioxide ($N_2O_4$) in an inert organic solvent to said compound or said compound dissolved in an inert organic solvent, at substantially anhydrous conditions, in the absence of catalyst. In the second method, the order of addition is reversed from the first method.

As regards the reaction between the alicyclic hydrocarbons having substituent groups and the liquid nitrogen dioxide ($N_2O_4$), there is no relevant prior art to the best knowledge of the present inventors.

It is therefore a primary object of the present invention to provide a novel method in the production of dibasic fatty acid from cycloalkanol or cycloalkanone having carbon atoms of from 5 to 12 ($C_5$–$C_{12}$), wherein the reaction completes without use of a catalyst, at a low temperature, under a normal pressure, and in a short period of time, the method being carried out in an easy way, and at a high rate of yield of a product.

It is a secondary object of the present invention to provide an effective method for producing dibasic fatty acids respectively corresponding to nitrate, nitrite, or oxime of cycloalkane having carbon atoms of from 5 to 12 ($C_5$-$C_{12}$).

According to the present invention, it is possible to carry it out either continuously or in batch to oxidizing and ring-opening cycloalkane derivatives, and yet with a rate of yield of the product and safety in the process which are comparable to, or surpassing those of the conventional method.

Furthermore, according to the present invention, it is possible to realize an effective ultilization of $NO_x$ which is a harmful component in the combustion waste gas from petroleum gas, natural gas, and so forth. That is to say, in the present method, cooled and liquefied $N_2O_4$ which has been produced from $NO_2$ converted by oxidizing $NO_x$ by the known method is used as the oxidizing agent. Or else, as the source of nitrogen dioxide, NO gas produced from a nitric acid producing apparatus operating under the ammonia contact oxidation method is used. The NO gas is oxidized, cooled and liquefied in the form of $N_2O_4$ for the purpose.

The foregoing objects, other objects as well as the reactions to take place in the method of the present invention will become more apparent and understandable from the following detailed description of the invention, when read in connection with several preferred examples thereof.

DESCRIPTION OF THE PREFERRED EMBODIMENT

In the following, hypothetical mechanisms of the oxidation reaction of cycloalkane derivatives having carbon atoms of from 5 to 12 ($C_5$-$C_{12}$) according to the present invention will be shown.

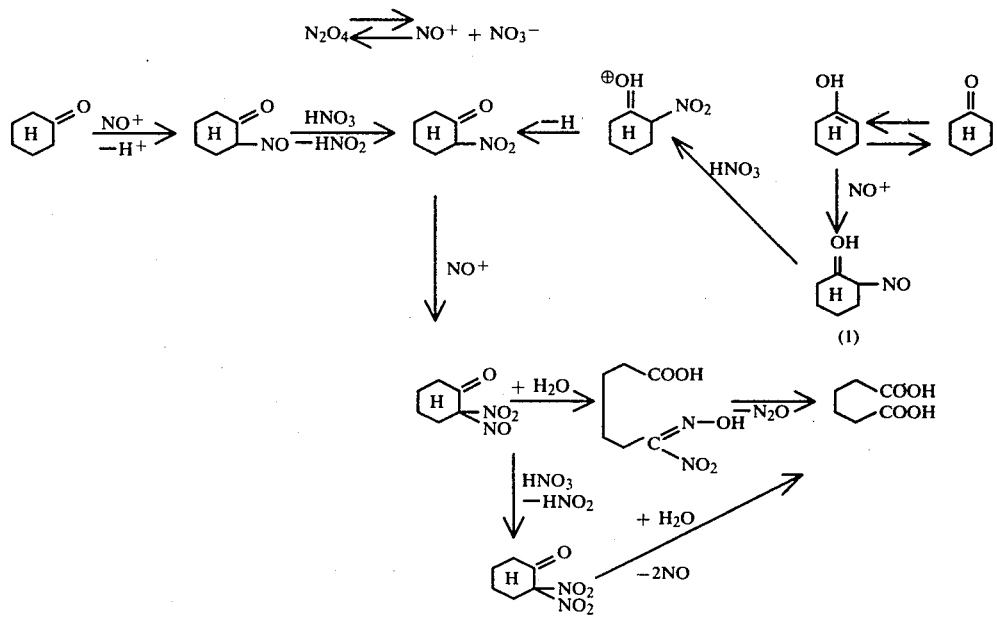

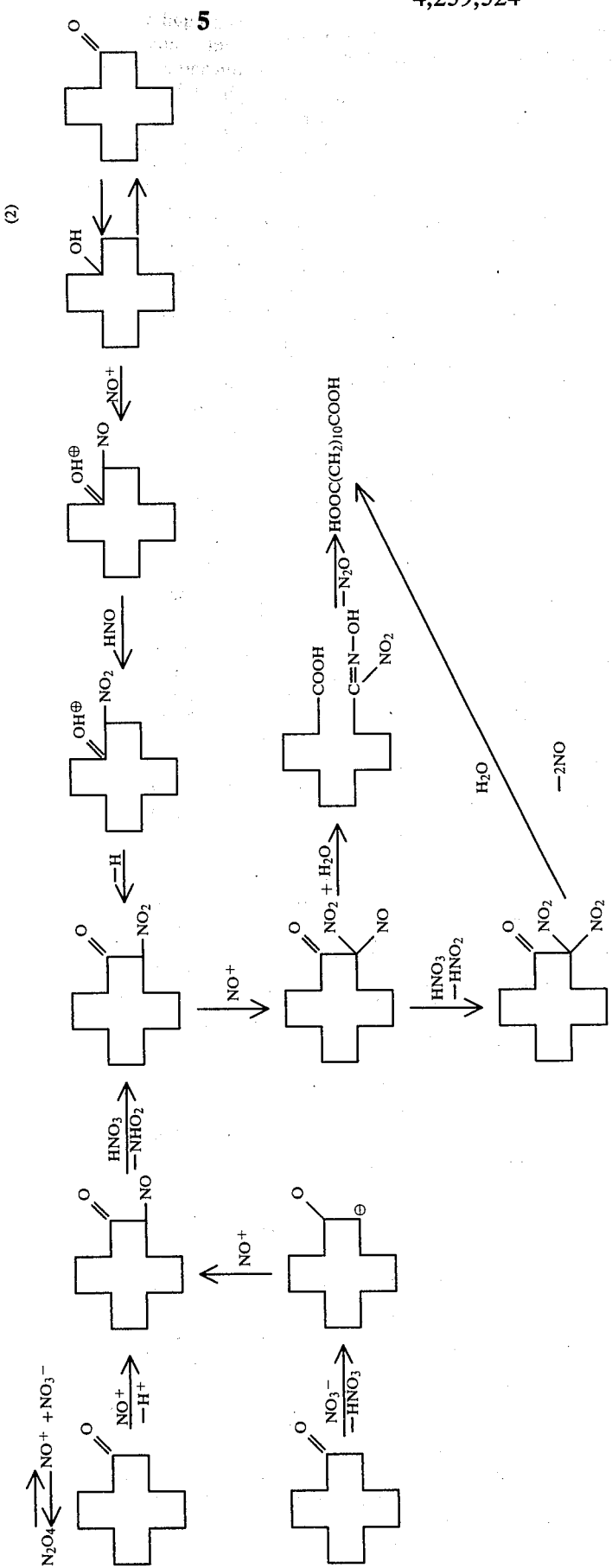

(3) The oxidation mechanism of cycloalkane nitrate, cycloalkane nitrite, cycloalkanone oxime, cycloalkanol, and so forth having carbon atoms of from 5 to 12 ($C_5$-$C_{12}$) has yet to be clarified, although the reaction is considered to proceed in a similar manner to the above equation after the compound is converted to cycloalkanone to open the ring of the compound and to produce the dibasic fatty acid.

While there has so far been no prior art of producing dibasic fatty acid by oxidizing and ring-opening an alicyclic hydrocarbon having a substituent group by the use of liquid nitrogen dioxide ($N_2O_4$), the present invention, especially the first method makes it important to produce the binary ionic additive, the product consisting of the liquid nitrogen dioxide ($N_2O_4$) as the oxidizing agent, and the reactant.

Now, when a relatively small quantity of the reactant is dripped into, and present in the liquid nitrogen dioxide ($N_2O_4$) in an excessive quantity, the equilibrium moves to the left side in the following equation, and the ionic reaction takes place.

Ionic
Reaction $\leftarrow (ANO^+)(NO_3^-) \rightleftarrows A + N_2O_4 \rightleftarrows A + 2NO_2 \rightleftarrows (A \cdot 2NO_2)$
(ionic property)  ↑ ↓ (molecular property)
$NO^+ + NO_3^-$
(where A denoton the reactant)

Inversely, when the liquid nitrogen dioxide ($N_2O_4$) is added to the reactant according to the second method of this invention it is also presumed to be the ionic reaction, although the difference from the former reaction in the reaction mechanism has not yet been verified.

Moreover, since the oxidation reaction is exothermic, it is necessary to remove heat of the reaction out of the reaction system for processing the main reaction while suppressing the side reaction. Therefore a good thermal conductive property of the reacting system is an important factor.

In taking consideration of the superiority of the thermal conductive property of liquid nitrogen dioxide ($N_2O_4$) than that of organic reacting substance, the first method of charging the reactant into the liquid nitrogen dioxide ($N_2O_4$) is superior in its rate of yield of the end product to the charging method which is reverse to the former, i.e., addition of the liquid nitrogen dioxide ($N_2O_4$) to the reactant, which is the second method of this invention. This is apparent when comparing the rate of yield of the end product in Example 1 to that in Example 10 and Example 6 to Example 11, respectively, described later.

Various reaction conditions for the present methods are: mol ratio between the liquid nitrogen dioxide ($N_2O_4$) and the substance to be reacted therewith, reaction temperature, rate of dripping of the substance to be reacted or the liquid nitrogen dioxide ($N_2O_4$), existence or non-existence of a solvent, kind of the solvent, existence or non-existence of impurities, and so forth. When it is necessary that the reaction should proceed relatively mildly depending on the end product to be obtained, there may be used the liquid nitrogen dioxide ($N_2O_4$) dissolved in an appropriate solvent, and/or the substance to be reacted as dissolved in an appropriate solvent.

In summary of the foregoing, the characteristic feature of the present invention consists in the method of carrying out the oxidation and ring-opening reaction of cycloalkane derivatives by the use of the liquid nitrogen dioxide ($N_2O_4$) paying particular attention to the versatility in the dissociation and equilibrium of the liquid nitrogen dioxide ($N_2O_4$), inter alia, taking particular advantage of the dissociation and equilibrium relative to the ionic reaction. Especially, when the substance to be reacted possesses high density in the electron accumulation, or the electron donating group is present in the reactant as the substituent group, the present invention provides an extremely advantageous reaction method. Moreover, the method of the present invention suggests the development in the de-nitration method of the waste gas containing oxygen and $NO_x$ by an organic substance.

In order to enable those persons skilled in the art to readily reduce the present invention into practice, the following preferred examples are presented. It should, however, be noted that these examples are merely illustrative and not restrictive, and that any change and modification may be made by those skilled in the art in respect of the various reaction conditions as mentioned in the foregoing without departing from the spirit and scope of the present invention as set forth in the appended claims.

EXAMPLE 1

(Snythesis of adipic acid by oxidation of cyclohexanone with liquid nitrogen dioxide ($N_2O_4$))

Approximately 0.5 ml of liquid nitrogen dioxide ($N_2O_4$) is placed in a reaction tube, to which 0.4752 g (4.66 m mol) of cyclohexanone is gradually added at a room temperature, about 18° C.-20° C., which is below the boiling point of $N_2O_4$. The reaction at its initial stage is very mild, and there appears to be almost no change in the reaction system; however, after lapse of 5 minutes, the reaction becomes abruptly active and terminates in 1 to 2 minutes. During the reaction, the reaction temperature is maintained at about 18° C.-20° C. by cooling the reaction tube.

The reaction mixture is substantially in solid form. After removal of $N_2O_4$, this reaction mixture is washed with benzene, whereby 0.5752 g (3.94 m mol) of pure adipic acid is obtained at a rate of yield of 85%. When the reaction is conducted at a temperature range of from 5° to 15° C., it can be proceeded fairly mildly.

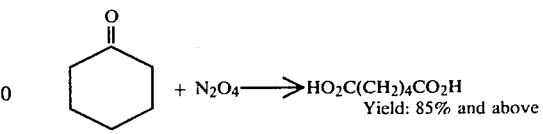
Yield: 85% and above

EXAMPLE 2

(Synthesis of glutaric acid by oxidation of cyclopentanone with liquid nitrogen dioxide ($N_{2l}O_4$))

To approximately 0.5 ml of liquid nitrogen dioxide ($N_2O_4$), there is gradually added 0.4683 g (5.58 m mol) of cyclopentanone. The reaction temperature is maintained at about 18° C.-20° C. as the same as in Example 1. Although the reaction is very mild at its initial stage, it becomes abruptly very active after lapse of 5 minutes and completes in about 1 to 2 minutes thereafter.

A solid white substance resulted from the reaction is washed with benzene after removal of $N_2O_4$, whereby crystals of pure glutaric acid is obtained in a quantity of 0.407 g (a rate of yield of 56%).

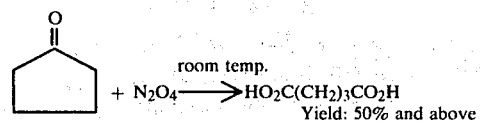

EXAMPLE 3

(Synthesis of adipic acid by oxidation of cyclohexanol with liquid nitrogen dioxide (N₂O₄))

0.8 ml of liquid nitrogen dioxide (N$_2$O$_4$) is placed in a reaction tube of a 20 ml capacity, and a solution of cyclohexanol, 0.954 g which is dissolved in 5 ml of n-hexane, is gradually added thereto at a room temperature. The reaction terminates in about 10 to 15 minutes, and during the reaction the reaction temperature is maintained at about 18° C.–25° C. Although the reaction proceeds very mildly throughout but it becomes retarded at a reacting temperature of 10° to 15° C.

When cyclohexanol is directly added to the liquid nitrogen dioxide, the reaction proceeds in a fairly violent manner.

After removal of the liquid nitrogen dioxide (N$_2$O$_4$) from a solid reaction mixture, it is washed with benzene, whereby substantially pure adipic acid is obtained in a quantity of 1.183 g (85% yield rate).

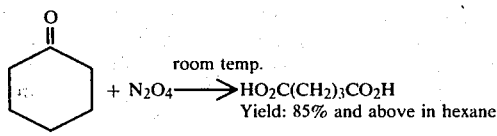

EXAMPLE 4

(Synthesis of 1, 10-decane dicarboxylic acid by oxidation of cyclododecanol with liquid nitrogen dioxide (N₂O₄))

When 1 g of cyclododecanol

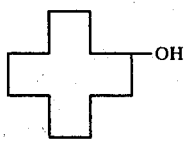

is added to 2 to 3 ml of liquid nitrogen dioxide (N$_2$O$_4$) at a room temperature about 18° C.–20° C., below the boiling point of N$_2$O$_4$, they react very violently. After completion of the reaction, N$_2$O$_4$ is removed from the reaction system to thereby obtain white crystals. When the white crystals are washed with benzene, 1,1 g of substantially pure 1,10-decane dicarboxylic acid HOOC(CH$_2$)$_{10}$COOH is obtained at a rate of yield of 90%.

EXAMPLE 5

(Synthesis of 1,10-decandicarboxylic acid, suberic acid and pimeric acid by oxidation of cyclododecanone, cyclooctanone and cycloheptanone, respectively, with liquid nitrogen dioxide (N₂O₄))

When 1 g of cyclododecanone

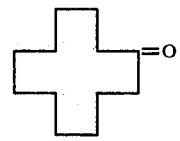

is added to 2 to 3 ml of liquid nitrogen dioxide (N$_2$O$_4$) at a room temperature, about 18° C.–20° C., they react violently. After termination of the reaction, N$_2$O$_4$ is removed and crystals are recovered therefrom. When the crystals are washed with benzene, there is obtained 1.1 g of substantially pure 1,10-decandicarboxylic acid at a rate of yield of 88%.

In the same manner as mentioned above, suberic acid HOOC(CH$_2$)$_6$COOH, and pimeric acid HOOC(CH$_2$)$_5$COOH are respectively obtained from cyclo-octanone and cycloheptanone at a rate of yield of 90%, respectively.

EXAMPLE 6

(Synthesis of adipic acid by oxidation of cyclohexanone oxime with liquid nitrogen dioxide (N₂O₄))

When 1 g of cyclohexanone oxime

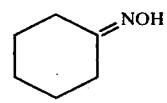

is added to 2 to 3 ml of liquid nitrogen dioxide (N$_2$O$_4$) at a room temperature about 18° C.–20° C., they react violently generating a flame, and then the reaction terminates. When 1 g of cyclohexanone oxime dissolved in 5 ml of dichloro-methane CH$_2$Cl$_2$ is gradually added to 2 to 3 ml of liquid N$_2$O$_4$ dissolved in 5 ml of CH$_2$Cl$_2$ at 0° C. and left for 30 minutes, after which both liquid N$_2$O$_4$ and CH$_2$Cl$_2$ are removed to obtain a product in the form of crystals. This product is then washed with benzene to yield 1.16 g of adipic acid HOOC(CH$_2$)$_4$COOH in crystal form at a rate of yield of 90%. The rate of yield is not changed when cyclohexanone oxime dissolved in CH$_2$Cl$_2$ is added to liquid N$_2$O$_4$ not dissolved in the solvent.

Besides CH$_2$Cl$_2$ as the solvent, CCl$_4$ and CHCl$_3$ are also used for the reaction, and the reaction proceeds in the same degree as is the case with using CH$_2$Cl$_2$ with the same rate of yield of the product.

EXAMPLE 7

(Synthesis of adipic acid by oxidation of cyclohexyl nitrite with liquid nitrogen dioxide (N₂O₄))

200 mg of cyclohexyl nitrite

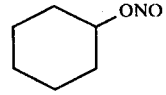

is gradually added to 10 ml of ice-cooled cyclohexane solution containing therein 1 to 2 ml of liquid N$_2$O$_4$. After termination of the reaction, both liquid N$_2$O$_4$ and cyclohexane are removed to obtain a product in crystal form. When the product is washed with benzene, 206 mg of adipic acid in white crystals is obtained at a rate of yield of 91%.

EXAMPLE 8

(Synthesis of adipic acid by oxidation of cyclohexyl nitrate with liquid nitrogen dioxide (N$_2$O$_4$))

200 mg of cyclohexyl nitrate

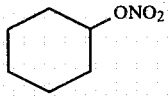

is gradually added to 10 ml of ice-cooled solution containing therein 1 to 2 ml of liquid N$_2$O$_4$. After termination of the reaction, both liquid N$_2$O$_4$ and cyclohexane are removed to obtain a product in crystal form. When the product is washed with benzene, 190 mg of adipic acid in white crystals is obtained. The rate of yield thereof is 95%.

EXAMPLE 9

(Synthesis of adipic acid by oxidation of cyclohexyl nitrate)

When 100 mg of cyclohexyl nitrate is added to 5 ml of dichloro-methane CH$_2$Cl$_2$ solution containing therein 1 to 2 ml of liquid N$_2$O$_4$ at a room temperature about 18° C.-20° C., they react very violently to produce a product in white crystals. After termination of the reaction, both liquid N$_2$O$_4$ and CH$_2$Cl$_2$ are removed, and the abovementioned white crystal product is washed with benzene, whereupon 97.9 mg of adipic acid in white crystals is obtained. The rate of yield thereof is 98%.

EXAMPLE 10

(Synthesis of adipic acid by oxidation of cyclohexanone with liquid nitrogen dioxide (N$_2$O$_4$)... second method)

2.8 m mol of cyclohexanone is dissolved into 25 ml of dichloro-methane CH$_2$Cl$_2$, and the mixture solution is maintained at a room temperature about 18° C.-20° C.

Then, 10 ml of CH$_2$Cl$_2$ solution containing 2 to 3 ml of liquid N$_2$O$_4$ is gradually added to the abovementioned cyclohexanone solution, and the batch is left for about 15 minutes at a room temperature to complete the reaction. After termination of the reaction, both liquid N$_2$O$_4$ and CH$_2$Cl$_2$ are removed, followed by washing of the residual reaction product with benzene, whereby adipic acid is obtained at a rate of yield of 52%.

EXAMPLE 11

(Synthesis of adipic acid by oxidation of cyclohexanone oxime with lliquid nitrogen dioxide (N$_2$O$_4$)... second method)

1.5 m mol of cyclohexanone oxime is dissolved into 25 ml of dichloro-methane CH$_2$Cl$_2$ and the solution is maintained at a room temperature about 18° C.-25° C.

Then, 10 ml of dichloro-methane CH$_2$Cl$_2$ containing therein 2 to 3 ml of liquid N$_2$O$_4$ is gradually added to the abovementioned cyclohexanone oxime and dichloromethane solution, and the batch is left for about 15 minutes at a room temperature to complete the reaction. After termination of the reacton, liquid N$_2$O$_4$ and the solvent are removed, and the reaction product is washed with benzene to thereby obtain adipic acid at a rate of yield of 25%.

When comparing Example 1 to Example 10 and Example 6 to Example 11, it is apparent that the first method of this inventon, i.e., Examples 1 and 6, is superior to the second method of this invention i.e. Examples 10 and 11, respectively. Further, the second method has been also conducted with respect to Examples 4, 5, 7, 8 and 9, and the corresponding dibasic fatty acids are obtained qualitatively.

Summarizing the effect of the method according to the present invention, the oxidation reaction of cycloalkane derivatives according to the present invention, can be conducted without use of the catalyst, under a normal pressure, and at a normal temperature. Moreover, the reaction is ionic and proceeds quickly and easily with high rate of yield and high purity of the end product, hence the post-treatment of the reaction system is quite easy.

What is claimed is:

1. A method for producing a dibasic fatty acid comprising oxidizing and ring-opening an alicyclic compound containing from about 5 to 12 carbon atoms by adding the compound to liquid N$_2$O$_4$, said oxidizing and ring-opening reaction being operated at a temperature below the boiling point of liquid N$_2$O$_4$ in the absence of catalyst, said alicyclic compound being selected from the group consisting of cycloalkanones, cycloalkanols, cycloalkylnitrates, cycloalkylnitrites and cycloalkanone oximes.

2. A method according to claim 1, in which an alicyclic compound is dissolved in an inert organic solvent, at substantially anhydrous conditions.

3. A method according to claim 1 in which liquid N$_2$O$_4$ is dissolved in an organic solvent, at substantially anhydrous conditions.

4. A method according to claim 1 in which each of said alicyclic compound and liquid N$_2$O$_4$ are dissolved in an organic solvent, at substantially anhydrous conditions.

* * * * *